United States Patent [19]

Dolhyj et al.

[11] 4,163,862

[45] Aug. 7, 1979

[54] PREPARATION OF UNSATURATED ACIDS

[75] Inventors: Serge R. Dolhyj, Parma; Ernest C. Milberger, Solon, both of Ohio

[73] Assignee: Standard Oil Company (Ohio), Cleveland, Ohio

[21] Appl. No.: 653,853

[22] Filed: Jan. 30, 1976

Related U.S. Application Data

[60] Continuation of Ser. No. 507,499, Sep. 13, 1974, which is a division of Ser. No. 409,693, Oct. 25, 1973, abandoned.

[51] Int. Cl.$^2$ .................... C07C 51/32; C07C 57/04
[52] U.S. Cl. .................................. 562/534; 252/432; 252/435; 252/437; 252/455 R; 252/462; 260/346.75; 560/208; 562/535
[58] Field of Search ............... 260/530 N; 252/437, 252/435, 462; 562/534, 535

[56] References Cited

U.S. PATENT DOCUMENTS

| | | | |
|---|---|---|---|
| 3,435,069 | 3/1969 | Bethell et al. | 260/530 N |
| 3,567,773 | 3/1971 | Yamaguchi et al. | 260/530 N |
| 3,875,220 | 4/1975 | White et al. | 260/530 N |
| 3,954,855 | 5/1976 | Wada et al. | 260/530 N |

*Primary Examiner*—Vivian Garner
*Attorney, Agent, or Firm*—D. J. Untener; H. D. Knudsen; L. W. Evans

[57] ABSTRACT

The present invention is a catalyst composition consisting of oxides or oxide complexes that contains catalytically significant amounts of cerium, tungsten, vanadium and molybdenum plus optionally one or more of Fe, Co, Ni, Zn, Cu, Mg, Mn, Bi, Ti, Zr, Sn, P, an alkali metal, an alkaline earth metal, lanthanum or an element of the lanthanoid series. These catalysts are especially useful for producing acrylic acid from acrolein and for producing methacrylic acid from methacrolein.

8 Claims, No Drawings

PREPARATION OF UNSATURATED ACIDS

CROSS REFERENCES TO RELATED APPLICATIONS

This is a continuation of Ser. No. 507,499, filed Sept. 19, 1974, which was a divisional of Ser. No. 409,693 filed Oct. 25, 1973, now abandoned.

BACKGROUND OF THE INVENTION

Catalyst compositions similar to those of the invention are known, see U.S. Pat. No. 3,567,773 which shows catalysts containing WVMo. The present invention adds cerium to these catalysts and obtains unexpectedly desirable catalysts for producing acrylic acid and methacrylic acid.

The production of acrylic acid by the oxidation of acrolein and the production of methacrylic acid by the oxidation of methacrolein are known in the art. With respect to these processes, the present invention employs the known art process but substitutes the catalysts of the invention for the catalysts of the art.

SUMMARY OF THE INVENTION

The present invention is a catalyst composition consisting of oxides or oxide complexes that contains catalytically significant amounts of cerium, tungsten, vanadium and molybdenum plus optionally one or more of Fe, Co, Ni, Zn, Cu, Mg, Mn, Bi, Ti, Zr, Sn, P, an alkali metal, an alkaline earth metal, lanthanum or an element of the lanthanoid series. These catalysts are especially effective for preparing acrylic acid from acrolein and the preparation of methacrylic acid from methacrolein. The catalysts are also highly effective for oxidation reactions such as the oxidation of butadiene to maleic anhydride and the oxidative esterification of unsaturated aldehydes to the corresponding unsaturated ester. The catalysts of the invention are highly reactive and are capable of very selectively oxidizing acrolein to acrylic acid at low temperatures with little or no acetic acid production.

The invention is the catalyst composition. The basic invention is a catalyst containing cerium, tungsten, vanadium and molybdenum. The other possible elements of the catalyst are optionally included.

As noted above, catalysts very similar to the catalysts of the invention are known, see for example U.S. Pat. No. 3,567,773. Moreover, catalysts of the general type of the catalysts are known and a person of ordinary skill in the art needs no more than the description of the elements in the catalyst to prepare catalysts claimed by the present invention. Thus, the broad description of the invention makes the catalysts of the invention available.

Normally, the catalysts of the invention are prepared by mixing the catalyst ingredients in the proper proportions in an aqueous mixture, drying the resulting aqueous slurry and calcining the product. The ingredients going into the preparation of the catalysts can be the oxides, halides, nitrates or other salts of the particular compound added. If a support is used, the material comprising the support is usually incorporated into the catalyst along with the other ingredients. After the catalyst ingredients have been combined to form an aqueous slurry, the slurry is evaporated to dryness, and the dried solid obtained is heated in the presence of air at temperatures between about 200° and 600° C. This calcination can take place outside of the catalytic reactor or an in situ activation could be utilized.

Although there are a number of preparations that could be used to make desirable catalysts of the invention, catalysts that contain molybdenum in a partially reduced state below hexavalent molybdenum are preferred. The preparation of catalysts of the invention containing reduced molybdenum is shown in the Specific Embodiments.

The broad composition of the catalyst is described above. With respect to the composition, there are certain preferred embodiments. Preferred are those catalysts wherein more than about 50% of the atoms, exclusive of oxygen and any support material, are molybdenum. Also, with respect to the broad description, those catalysts having no optional components or optional components of Fe, Ni, Co, Zn, Sn, Mn, Mg, Cu or mixture thereof are preferred.

In terms of a specific empirical formula, the catalysts of the invention are described by the following formula:

$$A_a Ce_b W_c V_d Mo_e O_x$$

wherein
A is Fe, Co, Ni, Zn, Cu, Mg, Mn, Bi, Ti, Zr, Sn, P, an alkali metal an alkaline earth metal, lanthanum, an element of the lanthanoid series or mixture thereof; and wherein:
  a is 0 to about 5;
  b, c and d are about 0.1 to about 10;
  e is a number of about 6 to about 16; and
  x is the number of oxygens required to satisfy the valence requirements of the other elements present.

Referring to the formula, preferred catalysts are designated when A is Fe, Ni, Co, Zn, Sn, Mn, Mg, Cu or mixture thereof and when a is greater than zero. Individual optional elements represented by A which are preferred are copper and cobalt.

In addition to the active catalytic ingredients, the catalysts of the invention may contain a support material. Suitable support materials include silica, alumina, zirconia, titania, silicon carbide, boron phosphate and the like. A preferred support material is silica.

As noted above, the catalysts of the invention are useful in a number of different oxidation reactions. Preferred among these reactions is the production of unsaturated acids from the corresponding unsaturated aldehyde. In such a process, acrylic acid or methacrylic acid is produced by reacting acrolein or methacrolein with molecular oxygen in the presence of steam at a temperature of about 200° to about 500° C. Of special interest is the preparation of acrylic acid from acrolein because of the extremely desirable results obtained.

The oxidation of unsaturated aldehydes to obtain the corresponding acid is well known in the art. Basically, the invention, with respect to the process, is the use of the new catalyst within the parameters of the known art process.

The known process involves the contacting of the unsaturated aldehyde with molecular oxygen in the presence of steam at a temperature of about 200° to about 500° C. The ratio of the reactants may vary widely with molar ratios of molecular oxygen to aldehyde of about 0.5 to about 5 moles normally being employed. Molecular oxygen is most conveniently added as air. The amount of steam may vary widely from the small amount generated in the reaction to 20 or more moles of steam per mole of aldehyde. In the preferred practice of the invention, about 1 to about 10 moles of steam are added to the reactant feed.

The reaction may be conducted in a fixed- or fluid-bed reactor using atmospheric, superatomspheric or subatmospheric pressure. The apparent contact time may vary considerably with contact times of a fraction of a second to 20 seconds or more normally being employed.

Using the catalyst of the invention, very desirable yields of unsaturated acid are obtained at low temperatures with the production of little or no acetic acid.

SPECIFIC EMBODIMENTS

Comparative Example A and Examples 1-6—Various base catalysts of the invention Various base catalysts of the invention were prepared and compared to a catalyst of U.S. Pat. No. 3,567,773. The catalysts were prepared as follows:

Comparative Example A

62% $W_{1.2}V_3Mo_{12}O_x$ and 38% $SiO_2$ This catalyst was prepared according to Example 6 of U.S. Pat. No. 3,567,773.

EXAMPLES 1 & 2

62% $Ce_2W_{1.2}V_3Mo_{12}O_x$ and 38% $SiO_2$ In 750 c.c. of hot distilled water, 14.62 g. ammonium metavanadate, 87.8 g. of ammonium molybdate and 13.48 g. of ammonium tungstate were dissolved. Separately, 45.68 g. of $(NH_4)_2Ce(NO_3)_6$ was dissolved in 100 c.c. of water and this solution was added to the first solution. A yellow precipitate was formed. About 15 minutes after the addition, 168.8 g. of 40% Nalco silica sol was added. The liquid was evaporated to a thick yellow paste. The paste was dried over night at 110° C. to give a light orange material. The catalyst was calcined in air at 400° C. for two hours.

EXAMPLE 3

$Ce_3W_{1.2}V_3Mo_{12}O_x$ In 500 c.c. of distilled water, 72.0 g. $MoO_3$, 11.36 g. of $V_2O_5$, 9.19 g. of tungsten metal and 21.51 g. of $CeO_2$ were slurried and refluxed for two hours. The color of the liquid turned to dark blue. The slurry was evaporated and dried over night at 110° C. to yield a gray-green solid. The catalyst was calcined as shown in Example 1.

EXAMPLE 4

$Ce_3W_{1.2}V_3Mo_{12}O_x$ As shown in Example 3, a slurry was formed and refluxed, except that no cerium compound was added. Separately, 43.03 g. of cerium acetate was dissolved in 400 c.c. of water and added to the slurry after reflux. The combined mixture was refluxed for an additional hour. The product was dried and calcined as shown above.

EXAMPLE 5

$CeW_{1.2}V_3Mo_{12}O_x$ The catalyst was prepared as shown in Example 4, except that 14.34 g. of cerium acetate was used.

EXAMPLE 6

$Ce_{0.5}W_{1.2}V_3Mo_{12}O_x$ The catalyst was prepared as shown in Example 4, except that 7.17 g. of cerium acetate was used.

The catalysts prepared above were placed in a reactor constructed of a 1.0 cm. inside diameter stainless steel tube having a reaction zone of 20 c.c. The reactor was heated in a split block furnace. The reactor was fed with a mixture of acrolein/air/steam in the molar ratio of 1/10/6. The temperature of the surrounding block and the apparent contact time are given in Table I. The results are also given in Table I using the following definitions.

$$\text{Single pass yield} = \frac{\text{moles of product recovered} \times 100}{\text{moles of acrolein fed}}$$

$$\text{Conversion} = \frac{\text{moles of acrolein reacted} \times 100}{\text{moles of acrolein fed}}$$

$$\text{Selectivity} = \frac{\text{moles of acrylic acid recovered} \times 100}{\text{moles of acrolein reacted}}$$

TABLE I

Comparison of CeWVMo with WVMo in the Preparation of Acrylic Acid

| Example | Catalyst | Temp., C. | C.T., Sec. | Single Pass Yield, % Acrylic Acid | Single Pass Yield, % Acetic Acid | Conversion, % | Selectivity, % |
|---|---|---|---|---|---|---|---|
| Comp. A | $W_{1.2}V_3Mo_{12}O_x$ | 274 | 1.8 | 80.4 | 6.3 | 99.6 | 80.7 |
| 1 | $Ce_2W_{1.2}V_3Mo_{12}O_x$ | 260 | 2.1 | 85.9 | 1.2 | 100 | 85.9 |
| 2 | " | 246 | " | 85.5 | 0 | 92.6 | 92.3 |
| 3 | $Ce_3W_{1.2}V_3Mo_{12}O_x$ | 232 | 2.3 | 94.0 | 0 | 100 | 94.0 |
| 4 | $Ce_3W_{1.2}V_3Mo_{12}O_x$ | 288 | 2.0 | 96.1 | 0 | 100 | 96.1 |
| 5 | $CeW_{1.2}V_3Mo_{12}O_x$ | 274 | 2.0 | 94.4 | 0 | 99.4 | 94.9 |
| 6 | $Ce_{0.5}W_{1.2}V_3Mo_{12}O_x$ | " | 2.0 | 91.7 | 0 | 100 | 91.7 |

EXAMPLES 7-11—CeWVMo catalysts containing optional elements.

Catalysts of the invention containing optional elements were prepared as follows:

EXAMPLE 7

$CoCe_2W_{1.2}V_3Mo_{12}O_x$ In the same manner shown by Example 3, except that 14.34 g. of $CeO_2$ was used, a slurry was prepared and refluxed for two hours. Separately, 10.38 g. of cobalt acetate was dissolved in warm water and added to the above slurry after reflux. The mixture was evaporated and calcined as shown above.

EXAMPLE 8

$Cu_2Ce_2W_{1.2}V_3Mo_{12}O_x$ The catalyst was prepared in the same manner, except the cobalt acetate was replaced with 16.64 g. of copper acetate dissolved in 150 c.c. of water.

EXAMPLE 9

30% $Cu_2Ce_2W_{1.2}V_3Mo_{12}O_x$ and 70% Alundum A total of 10.71 g. of the catalyst of Example 8 having a particle size of less than 50 mesh was coated on 20 to 30 mesh Alundum particles by rolling the partially wet Alundum particles in the catalyst powder in a cylindrical vessel. A strongly adhering coat of catalytic ingredients on the surface of the Alundum resulted. These catalyst particles were dried and calcined as shown above.

EXAMPLE 10

$Sn_{0.5}Ce_2W_{1.2}V_3Mo_{12}O_x$ In 500 c.c. of water 72.0 g. of $MoO_3$, 11.36 g. of $V_2O_5$, 3.13 g. of $SnO_2$, 9.19 g. of tungsten metal and 14.34 g. of $CeO_2$ were slurried and refluxed for two hours. The slurry was evaporated and the catalyst was dried and calcined as shown above.

EXAMPLE 11

$Sn_{0.5}Ce_3W_{1.2}V_3Mo_{12}O_x$ The catalyst was prepared as described in Example 10, except that 21.51 g. of $CeO_2$ was used.

The production of acrylic acid from acrolein was conducted with these catalysts in the same manner as shown in the examples above. The results of these experiments are given in Table II.

TABLE II
Production of Acrylic Acid Using Catalysts Containing Optional Elements

| Example | Catalyst | Temp., °C. | C.T., Sec. | Single Pass Yield, % Acrylic Acid | Single Pass Yield, % Acetic Acid | Conversion, % | Selectivity, % |
|---|---|---|---|---|---|---|---|
| 7 | $CoCe_2W_{1.2}V_3Mo_{12}O_x$ | 274 | 2.1 | 94.8 | 0.2 | 100 | 94.8 |
| 8 | $Cu_2Ce_2W_{1.2}V_3Mo_{12}O_x$ | 232 | 2.2 | 97.0 | 0 | 100 | 97.0 |
| 9 | 30% $Cu_2Ce_2W_{1.2}V_3Mo_{12}O_x$ 70% Alundum | 246 | 2.2 | 97.6 | 0 | 100 | 97.6 |
| 10 | $Sn_{0.5}Ce_2W_{1.2}V_3Mo_{12}O_x$ | 232 | 2.1 | 92.6 | 0 | 100 | 92.6 |
| 11 | $Sn_{0.5}Ce_3W_{1.2}V_3Mo_{12}O_x$ | 232 | 2.3 | 94.0 | 0 | 100 | 94.0 |

In the same manner as shown by the examples above, other catalysts of the invention containing different amounts of cerium and different optional elements, such as Fe, Mn, Ni, Mg and the like, are used to produce acrylic acid. Moreover, promoted catalysts containing various amounts of tungsten, vanadium and molybdenum are used.

Also using the catalysts of the invention, maleic anhydride, methacrylic acid or acrylates are made by known oxidation reactions.

We claim:

1. In the process for the production of acrylic acid or methacrylic acid by contacting acrolein or methacrolein with molecular oxygen in the presence of steam and a catalyst at a temperature of 200° to about 500° C., the improvement comprising using as the catalyst a catalyst composition having the empirical formula:

$$A_aCe_bW_cV_dMo_eO_x$$

wherein
  A is Fe, Co, Ni, Zn, Cu, Mg, Mn, Bi, Ti, Zr, Sn, an alkali metal, an alkaline earth metal, lanthanum, an element of the lanthanoid series or mixture thereof;
and wherein
  a is 0 to about 5;
  b, c and d are about 0.1 to about 10;
  e is a number of about 6 to about 16; and
  x is the number of oxygens required to satisfy the valence requirements of the other elements present.

2. The process of claim 1 wherein A in said catalyst is Fe, Ni, Co, Zn, Sn, Mn, Mg, Cu or mixture thereof and a is greater than zero.

3. The process of claim 2 wherein A in said catalyst is copper.

4. The process of claim 2 wherein A in said catalyst is cobalt.

5. The process of claim 1 wherein said catalyst contains no optional components.

6. The process of claim 1 wherein more than about 50 percent of the atoms of said catalyst, exclusive of oxygen and any support material, are molybdenum.

7. The process of claim 1 wherein acrylic acid is prepared from acrolein.

8. The process of claim 1 wherein said catalyst is $Ce_3W_{1.2}V_3Mo_{12}O_x$.

* * * * *